(12) United States Patent
Funazukuri et al.

(10) Patent No.: US 10,733,992 B2
(45) Date of Patent: Aug. 4, 2020

(54) COMMUNICATION DEVICE, COMMUNICATION ROBOT AND COMPUTER-READABLE STORAGE MEDIUM

(71) Applicant: TOYOTA JIDOSHA KABUSHIKI KAISHA, Toyota-shi (JP)

(72) Inventors: Mina Funazukuri, Toyota (JP); Shintaro Yoshizawa, Nagoya (JP); Wataru Kaku, Nagoya (JP); Hitoshi Yamada, Nagakute (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 126 days.

(21) Appl. No.: 16/002,506

(22) Filed: Jun. 7, 2018

(65) Prior Publication Data
US 2018/0366121 A1    Dec. 20, 2018

(30) Foreign Application Priority Data

Jun. 14, 2017   (JP) ................................. 2017-116912

(51) Int. Cl.
*G06N 3/00*        (2006.01)
*G10L 15/22*       (2006.01)
(Continued)

(52) U.S. Cl.
CPC ............ *G10L 15/22* (2013.01); *A61B 5/0077* (2013.01); *A61B 5/165* (2013.01); *B25J 11/001* (2013.01);
(Continued)

(58) Field of Classification Search
CPC .................................. G06F 3/01; G06N 3/008
See application file for complete search history.

(56) References Cited

U.S. PATENT DOCUMENTS 6,570,555 B1 * 5/2003 Prevost ..................... G06F 3/01
                                                           345/156
9,199,122 B2   12/2015 Kaleal, III et al.
(Continued)

FOREIGN PATENT DOCUMENTS

EP   1 988 493 A1   11/2008
EP   2 933 067 A1   10/2015
(Continued)

*Primary Examiner* — Feng-Tzer Tzeng
(74) *Attorney, Agent, or Firm* — Oblon, McClelland, Maier & Neustadt, L.L.P.

(57) ABSTRACT

A communication device including: an utterance acquisition part configured to acquire an utterance of a user to a character; an information acquisition part configured to acquire information different from the utterance; a voice generation part configured to generate a response voice to be emitted by the character based on a content of the utterance acquired by the utterance acquisition part; and an expression generation part configured to generate a response expression to be expressed by a face portion of the character based on the content of the utterance acquired by the utterance acquisition part, wherein when the information is acquired from the information acquisition part, the expression generation part generates the response expression using the information together with the content of the utterance, the response expression generated when the information is acquired being different from a response expression generated when the information is not acquired.

11 Claims, 14 Drawing Sheets

(51) Int. Cl.
*G10L 25/63* (2013.01)
*G10L 13/04* (2013.01)
*A61B 5/00* (2006.01)
*A61B 5/16* (2006.01)
*B25J 11/00* (2006.01)

(52) U.S. Cl.
CPC ........ *B25J 11/0005* (2013.01); *B25J 11/0015* (2013.01); *G06N 3/008* (2013.01); *G10L 13/043* (2013.01); *G10L 25/63* (2013.01); *A61B 2560/0242* (2013.01); *Y10S 901/46* (2013.01); *Y10S 901/47* (2013.01)

(56) References Cited

U.S. PATENT DOCUMENTS

| | | | | |
|---|---|---|---|---|
| 2001/0020837 | A1* | 9/2001 | Yamashita | B25J 13/003 |
| | | | | 318/567 |
| 2002/0077726 | A1 | 6/2002 | Thorisson | |
| 2008/0119959 | A1 | 5/2008 | Park et al. | |
| 2008/0255702 | A1 | 10/2008 | Lin | |
| 2009/0138262 | A1* | 5/2009 | Agarwal | H04M 3/4938 |
| | | | | 704/235 |
| 2010/0118163 | A1* | 5/2010 | Matsugu | G03B 17/16 |
| | | | | 348/231.99 |
| 2015/0038806 | A1 | 2/2015 | Kaleal, III et al. | |
| 2015/0126826 | A1 | 5/2015 | Kaleal, III et al. | |
| 2015/0314454 | A1 | 11/2015 | Breazeal et al. | |
| 2016/0151917 | A1 | 6/2016 | Faridi et al. | |
| 2016/0171979 | A1 | 6/2016 | Breazeal et al. | |
| 2016/0193732 | A1 | 7/2016 | Breazeal et al. | |
| 2016/0199977 | A1 | 7/2016 | Breazeal | |
| 2016/0317100 | A1 | 11/2016 | Kaleal, III et al. | |
| 2016/0375578 | A1 | 12/2016 | Zhu et al. | |
| 2017/0105662 | A1* | 4/2017 | Silawan | A61B 5/14542 |
| 2017/0148434 | A1 | 5/2017 | Monceaux et al. | |
| 2018/0168518 | A1* | 6/2018 | Kaleal, III | A61B 5/021 |
| 2019/0095775 | A1* | 3/2019 | Lembersky | G06K 9/00302 |

FOREIGN PATENT DOCUMENTS

| | | | | |
|---|---|---|---|---|
| FR | 2874724 A1 * | 3/2006 | | G06T 13/40 |
| JP | 2013-239914 A | 11/2013 | | |
| JP | 5499924 | 5/2014 | | |
| JP | 5624100 | 11/2014 | | |
| JP | 2016-193466 | 11/2016 | | |
| KR | 10-2017-0055040 A | 5/2017 | | |

* cited by examiner

COMMUNICATION DEVICE, COMMUNICATION ROBOT AND COMPUTER-READABLE STORAGE MEDIUM

INCORPORATION BY REFERENCE

The disclosure of Japanese Patent Application No. 2017-116912 filed on Jun. 14, 2017 including the specification, drawings and abstract is incorporated herein by reference in its entirety.

BACKGROUND

1. Technical Field

The disclosure relates to a communication device, a communication robot, and a computer-readable storage medium.

2. Description of Related Art

A communication device has been used that outputs a response sentence and a facial expression according to the contents of a user's voice (see, e.g., Japanese Unexamined Patent Application Publication No. 2016-193466 (JP 2016-193466 A)).

SUMMARY

In related communication devices, when the same voice content is input from a user, the same response sentence and the same facial expression are output. Thus, in many cases, the communication device lacks variation causing the user to lose interest in the communication device.

In order to solve such problems, the disclosure provides a communication device or the like that presents many different variations to a facial expression indicated by a character so that the character shows various facial expressions depending on a situation even for the same sentence.

A first aspect of the disclosure relates to a communication device that allows a character to talk with a user. The communication device includes an utterance acquisition part, an information acquisition part, a voice generation part, and an expression generation part. The utterance acquisition part is configured to acquire an utterance of the user to the character. The information acquisition part is configured to acquire information different from the utterance. The voice generation part is configured to generate a response voice to be emitted by the character based on a content of the utterance acquired by the utterance acquisition part. The expression generation part is configured to generate a response expression to be expressed by a face portion of the character based on the content of the utterance acquired by the utterance acquisition part. When the information is acquired from the information acquisition part, the expression generation part generates the response expression using the information together with the content of the utterance, the response expression generated when the information is acquired being different from a response expression generated when the information is not acquired.

With this configuration, for example, a facial expression expressed by the face portion of the character can be made different between when an emotion read from a facial expression of the user is taken into account and when the emotion is not taken into account. Therefore, even if the utterance of the user is the same, the facial expression expressed by the face portion of the character is rich in variation. It can be expected that the user has increased attachment to the character without getting tired of the dialogue.

The communication device according to the first aspect may further include a database configured to store a plurality of the response expressions data associated with a plurality of emotions, respectively. The expression generation part may select, from the database, the response expression associated with a third emotion that is determined according to a combination of a first emotion and a second emotion, the first emotion being estimated based on the content of the utterance and the second emotion being estimated based on the information acquired by the information acquisition part. In this way, by combining the differently estimated emotions, it is possible to accurately estimate an emotion of the user.

In the communication device according to the first aspect, in the database, the plurality of emotions may be associated with the plurality of the response expressions, respectively, based on a Russell's circumplex model. The expression generation part may determine the third emotion based on a sum of a first vector corresponding to the first emotion in the Russell's circumplex model and a second vector corresponding to the second emotion in the Russell's circumplex model. With such a configuration, the emotion of the user can be calculated more quantitatively.

In the communication device according to the first aspect, the expression generation part may select, from the database, the response expression corresponding to a fourth emotion that approximates the third emotion in a predetermined range. By giving a slight fluctuation to the emotion to be determined, it is possible to enrich a change in the facial expression of the face portion.

In the communication device according to the first aspect, when generating two response expressions consecutively, the expression generation part may generate at least one interpolation response expression between the two response expressions, the at least one interpolation response expression interpolating the two response expressions. For example, even if a facial expression to be displayed is changed significantly, the user does not feel the change is awkward when an intermediate facial expression is inserted and displayed.

In the communication device according to the first aspect, the information acquisition part may include an imaging part configured to capture an image of the user. The information acquisition part may include a biometric sensor configured to acquire biological information of the user. The information acquisition part may include an environmental sensor configured to acquire environmental information of a surrounding environment of the communication device. By using various sensors, it is possible to estimate the emotion of the user more accurately.

The communication device according to the first aspect may further include a state acquisition part configured to acquire an internal state of a character device that embodies the character. The expression generation part may generate the response expression based on the internal state acquired by the state acquisition part in addition to the content of the utterance and the information. With this configuration, not only the facial expression expressed by the face portion is determined in accordance with the emotion of the user, but also the facial expression appears as if the character shows its own emotion. Therefore, the user gets more attachment to the character.

A second aspect of the disclosure relates to a communication robot including the communication device according to the first aspect and the face portion. The face portion is configured to express the response expression generated by the expression generation part. When the communication device is embodied as, for example, a robot imitating an animal, the user can have a sense of the robot being like a pet and having more of an attachment to the robot.

A third aspect of the disclosure relates to a computer-readable storage medium including a memory part configured to store a communication control program to be executed by a computer of a communication device that allows a character to talk with a user. When the communication control program is executed by the computer, the computer executes an utterance acquisition step, an information acquisition step, a voice generation step, and an expression generation step. In the utterance acquisition step, an utterance of the user to the character is acquired. In the information acquisition step, information different from the utterance is acquired. In the voice generation step, a response voice to be emitted by the character is generated based on a content of the utterance acquired in the utterance acquisition step. In the expression generation step, a response expression to be expressed by a face portion of the character is generated based on the content of the utterance acquired in the utterance acquisition step. In the expression generation step, when the information is acquired, the response expression is generated using the information together with the content of the utterance, the response expression generated when the information is acquired being different from a response expression generated when the information is not acquired.

With this configuration, for example, a facial expression expressed by the face portion of the character can be made different between when an emotion read from a facial expression of the user is taken into account and when the emotion is not taken into account. Therefore, even if the utterance of the user is the same, the facial expression expressed by the face portion of the character is rich in variation. It can be expected that the user has increased attachment to the character without getting tired of the dialogue.

The above summary of the disclosure does not enumerate all the necessary features of the disclosure. In addition, the sub-combinations of these feature groups are also a part of the disclosure.

With the disclosure, it is possible to provide a communication device or the like that allows a character to show, even for the same dialogue, various expressions depending on the situation.

BRIEF DESCRIPTION OF THE DRAWINGS

Features, advantages, and technical and industrial significance of exemplary embodiments will be described below with reference to the accompanying drawings, in which like numerals denote like elements, and wherein.

DETAILED DESCRIPTION OF EMBODIMENTS

Hereinafter, the disclosure will be described through embodiments of the disclosure, but the disclosure defined in the claims is not limited to the following embodiments. In addition, all of the configurations described in the embodiments are not necessarily indispensable as means for solving the problem.

Figure 1:
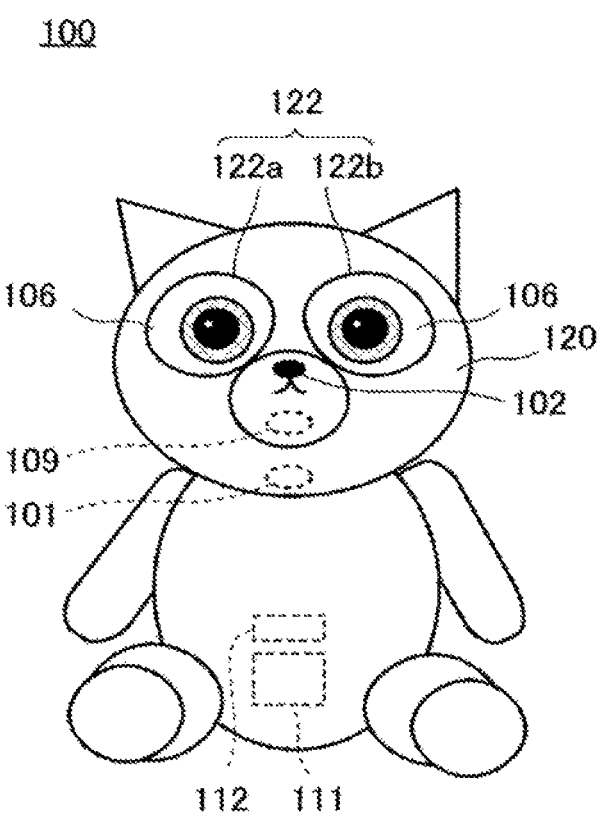
FIG. 1 is a schematic diagram of a robot according to a first embodiment.

FIG. 1 is a schematic diagram of a robot 100 according to a first embodiment. The robot 100 is a robot as a communication device that performs voice dialogue with a human user. The robot 100 is a character device that embodies a character and changes an expression of eyes in accordance with the dialogue.

The robot 100 imitates an animal in appearance and has a face portion 120. The face portion 120 is provided with an eye portion 122 (a right eye 122a and a left eye 122b) at a position that allows a user to recognize the eye portion 122 as the eyes. A structure of the eye portion 122 will be described in detail later. Behind each of the right eye 122a and the left eye 122b, a display panel 106, such as a liquid crystal panel or an organic EL panel, for example, is installed.

At a position of a nose of the robot 100, a camera 102 is arranged in an unnoticeable manner. The camera 102 includes, for example, a CMOS sensor, and functions as an imaging part that acquires an image for recognizing an external environment. At a position of a mouth of the robot 100, a speaker 109 is arranged in a hidden state. The speaker 109 functions as an utterance output part that emits a voice generated by the robot 100. The user feels as if the robot 100 is talking due to the voice output from the position of the mouth. In addition, a microphone 101 is arranged in a hidden state at any position of the face portion 120. The microphone 101 has a function of collecting a user's uttered voice or the like.

The robot 100 is operated by electric power supplied from a battery 111. The battery 111 is, for example, a lithium-ion battery. A battery monitoring part 112 is a circuit unit that monitors a remaining capacity of the battery 111 by, for example, an impedance track method.

Figure 2:
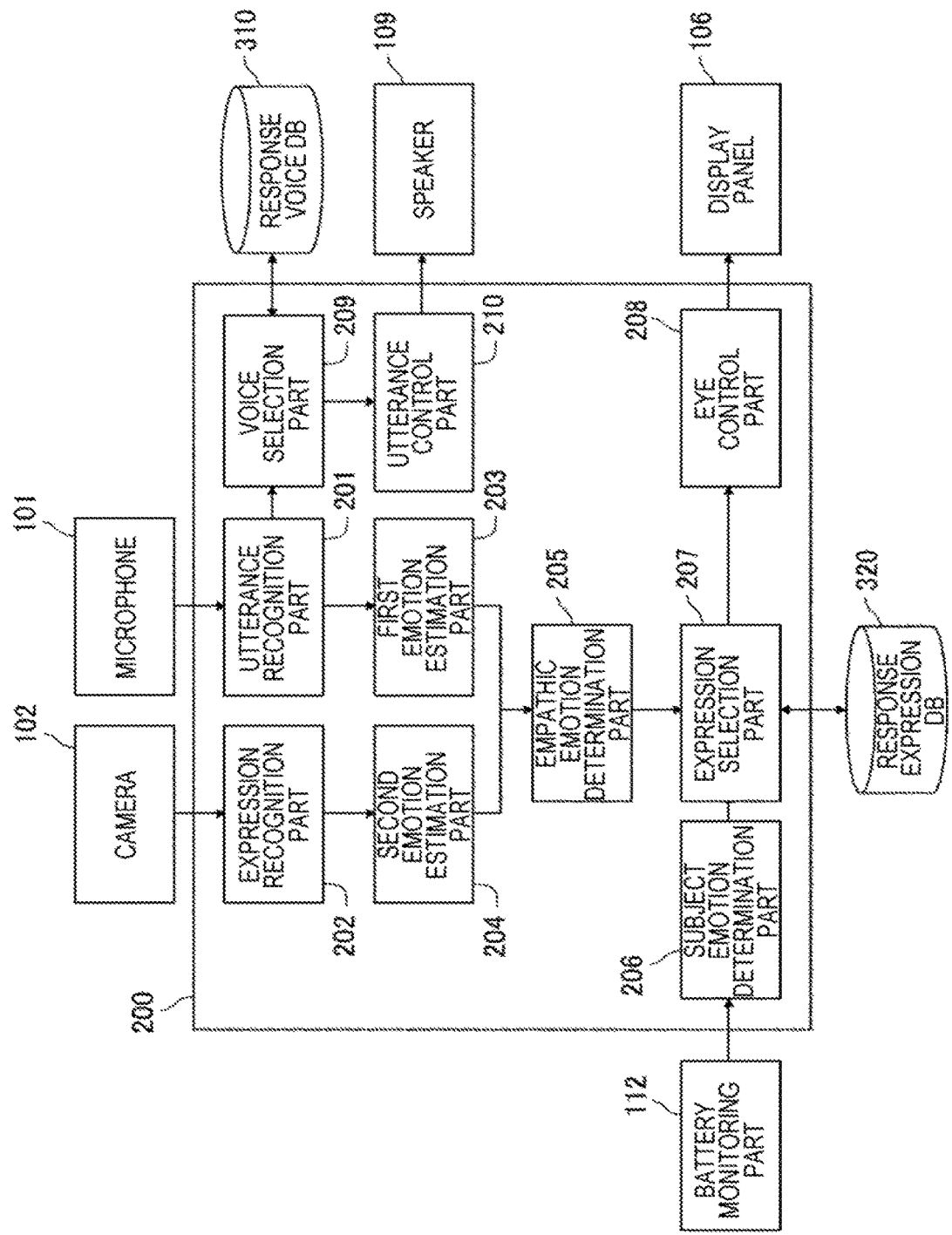
FIG. 2 is a system configuration diagram of the robot.

FIG. 2 is a system configuration diagram of the robot 100. The robot 100 includes, as main system components, the microphone 101, the camera 102, the display panel 106, the speaker 109, the battery monitoring part 112, a control part 200, a response voice DB 310, and a response expression DB 320. The control part 200 is configured by, for example, a CPU. The control part 200 operates as a function execution part for executing each function and mainly operates as an utterance recognition part 201, an expression recognition part 202, a first emotion estimation part 203, a second emotion estimation part 204, an empathic emotion determination part 205, a subject emotion determination part 206, an expression selection part 207, an eye control part 208, a voice selection part 209, and a utterance control part 210.

As a main function, the microphone 101 collects the uttered voice of the user who is the conversation partner of the robot 100. The microphone 101 converts the collected user's uttered voice into a voice signal and delivers the voice signal to the utterance recognition part 201. As a main function, the camera 102 captures an image of a face of the user facing the robot 100. The camera 102 converts the captured face image of the user into an image signal and delivers the image signal to the expression recognition part 202.

The speaker 109 receives a voice signal converted by the utterance control part 210 and outputs a response voice as a sound. The display panel 106 receives an image signal converted by the eye control part 208 and displays a pattern corresponding to a response expression. The battery monitoring part 112 detects the remaining capacity of the battery 111 and delivers a detection signal to the subject emotion determination part 206. The battery monitoring part 112 is an example of a state acquisition part that acquires an internal state of the robot 100.

The response voice DB 310 is a response voice database connected to the voice selection part 209 and is configured by, for example, a recording medium such as a hard disc drive. The response voice DB 310 is organized, for example, as a corpus. Individual terms are stored with reproducible utterance data. The response expression DB 320 is a response expression database connected to the expression selection part 207 and is configured by, for example, a recording medium such as a hard disk drive. The response expression DB 320 is organized, for example, as a Russell's circumplex model. The response expression DB 320 stores concrete image data of eye expressions, emotions indicated by the eye expressions, and degrees of the emotions in association with one another. Details will be described later.

The utterance recognition part 201 analyzes the voice signal received from the microphone 101 and recognizes the utterance of the user. The utterance recognition part 201 has a function as an utterance acquisition part that acquires a user's utterance toward the robot 100 in cooperation with the microphone 101. Specifically, the utterance recognition part 201 recognizes the user's utterance contents by a general voice recognition technique and analyzes prosody of the utterance. The prosody indicates physical characteristics of the utterance when the utterance is captured as sound waves. The utterance recognition part 201 calculates, for example, a center frequency, a frequency band, and a maximum value and average value of amplitude as the physical characteristics in a mass of sound waves emitted by the user. The utterance recognition part 201 delivers the recognized utterance contents to the voice selection part 209. In addition, the utterance recognition part 201 delivers the analyzed prosody to the first emotion estimation part 203.

The first emotion estimation part 203 extracts a change in amplitude level, an intonation of ending, and the like from the prosody received from the utterance recognition part 201, and estimates a type of the user's emotion and a degree of the user's emotion. The type and degree of the estimated emotion will be described in detail later. The type and degree of a first emotion estimated from the utterance of the user are delivered to the empathic emotion determination part 205.

The first emotion estimation part 203 may correct the type and degree of the user's emotion in consideration of an attribute of an uttered word. An attribute of a word indicates which emotion the word is usually used to express. For example, the word "happy" has an attribute of "contented." When the user utters "happy," the first emotion estimation part 203 brings the type of the estimated emotion to the "contented" side.

The expression recognition part 202 analyzes the image signal received from the camera 102 and recognizes a facial expression of the user. The expression recognition part 202 functions as an information acquisition part that, in cooperation with the camera 102, acquires the facial expression of the user as information different from the user's utterance. Specifically, the expression recognition part 202 extracts feature points from the face image of the user by a general face recognition technique, and calculates an expression feature amount such as positions of the feature points, inclinations of line segments connecting adjacent feature points, the number of feature points, and the like. The expression recognition part 202 delivers the calculated expression feature amount to the second emotion estimation part 204.

The second emotion estimation part 204 extracts, for example, a size of pupils, a degree of descent of outer eye corners, a degree of rise of mouth corners, presence or absence of perspiration, a degree of wrinkles, and the like from the expression feature amount received from the expression recognition part 202, and estimates the type and degree of the emotion of the user. The type and degree of the estimated emotion will be described in detail later. The type and degree of a second emotion estimated from the user's facial expression are delivered to the empathic emotion determination part 205.

When the user does not face the camera 102 or the face image is dark, the expression recognition part 202 cannot calculate the expression feature amount, and the second emotion estimation part 204 cannot estimate the type and degree of the second emotion. In such a case, the second emotion estimation part 204 delivers a signal indicating a fact that the second emotion cannot be generated to the empathic emotion determination part 205.

The empathic emotion determination part 205 combines the type and degree of the first emotion received from the first emotion estimation part 203 and the type and degree of the second emotion received from the second emotion estimation part 204, and determines a type and degree of an empathic emotion to be expressed by the robot 100 to the user. A specific procedure of determining the type and degree of the empathic emotion will be described in detail later. The type and degree of the empathic emotion are delivered to the expression selection part 207. In addition, upon receiving from the second emotion estimation part 204 the signal indicating the fact that the second emotion cannot be generated, the empathic emotion determination part 205 determines the type and degree of the first emotion as the type and degree of the empathic emotion.

The subject emotion determination part 206 converts a level of the detection signal received from the battery monitoring part 112 into a type and degree of a subject emotion of the robot 100 associated with the level of the detection signal and delivers the type and degree of the subject emotion to the expression selection part 207. The subject emotion is a certain emotion that is associated, in a pseudo manner, with a parameter indicating a state of the robot 100 (in this case, the remaining capacity of the battery). By representing an expression determined by the type and degree of the subject emotion, the robot 100 may indirectly show its own state to the external world. Specific association of the parameter with emotions and selection of the expression will be described later.

The expression selection part 207 acquires, from the response expression DB 320, image data of an expression that corresponds to the type and degree of the empathic emotion received from the empathic emotion determination part 205. In this case, the empathic emotion determination part 205 and the expression selection part 207 cooperate with each other and function as an expression generation part that generates a response expression to be expressed on the face portion 120 based on the user's utterance contents and facial expression. Alternatively, depending on conditions, the expression selection part 207 combines the type and degree of the subject emotion received from the subject emotion determination part 206 with the type and degree of the empathic emotion, and acquires, from the response expression DB 320, image data of an expression that corresponds to a result of the combination. Alternatively, under a situation where the user is not speaking or the like, the expression selection part 207 acquires, from the response expression DB 320, image data of an expression that corresponds only to the type and degree of the subject emotion received from the subject emotion determination part 206. The expression selection part 207 delivers the image data acquired from the response expression DB 320 to the eye control part 208. The eye control part 208 converts the image data received from the expression selection part 207 into an image signal capable of being displayed on the display panel 106 and delivers the image signal to the display panel 106.

The voice selection part 209 selects a sentence suitable for a conversation against the user's utterance contents recognized by the utterance recognition part 201, collects utterance data corresponding to the selected sentence from the response voice DB 310, and outputs the utterance data to the utterance control part 210. The utterance control part 210 converts the received utterance data into a voice signal and delivers the voice signal to the speaker 109. The voice selection part 209 and the utterance control part 210 cooperate with each other and function as a voice generation part that generates a response voice based on the user's utterance contents. The voice selection part 209 may change the sentence to be selected, by taking into consideration the emotion estimated by the first emotion estimation part 203. For example, when the first emotion estimation part 203 estimates the user's emotion as "sad", the voice selection part 209 may change the sentence to a sentence of encouraging content. By considering the emotion that the user puts in the utterance in this way, it is possible to expect deeper communication. However, it is preferable not to take into account the emotion estimated by the second emotion estimation part 204. As will be described later, the response voice generated by the robot 100 is rich in variations in combination with the response expression, when the emotion estimated by the second emotion estimation part 204 is not considered.

Figure 3:
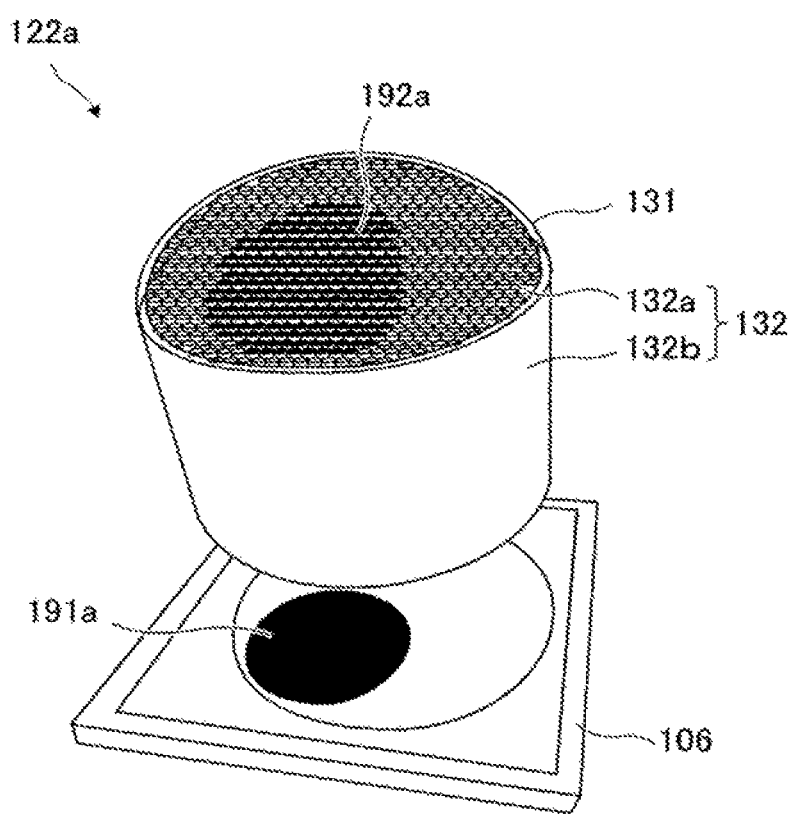
FIG. 3 is a perspective view showing a structure of a right eye.

FIG. 3 is a perspective view showing a structure of the right eye 122a. The left eye 122b also has the same structure as the right eye 122a. The display panel 106 of each of the right eye 122a and the left eye 122b is controlled by the eye control part 208.

The right eye 122a is mainly composed of a translucent cover 131, an optical fiber bundle 132, and the display panel 106. The translucent cover 131 is molded with, for example, transparent polycarbonate, and plays a role as an exterior material of the face portion 120. When a robot imitates an animal or a human being, eyes having a curved surface are natural and easily accepted by the user. Therefore, in the robot 100 according to the present embodiment, the translucent cover 131 corresponding to the surface of the eyes is formed into a curved surface bulging outward.

At an inner side of the right eye 122a, the display panel 106 that displays a pattern representing an expression of the right eye is installed. A display surface of the display panel 106 is a planar surface. In addition, the display surface has a size encompassing an outer peripheral circumference of the translucent cover 131. FIG. 3 shows a state in which the display panel 106 displays a display right-eye image 191a that is a pattern composed of a black part of the eye biasedly superimposed on a white part of eye having a size corresponding to the outer peripheral circumference of the translucent cover 131. Each pattern to be displayed is stored as image data in the response expression DB 320, read out by the expression selection part 207, converted into an image signal by the eye control part 208, and displayed on the display panel 106.

The inner curved surface of the translucent cover 131 and a surface of the display panel 106 are connected by the optical fiber bundle 132. The optical fiber bundle 132 transmits the display right-eye image 191a displayed on the display panel 106 to the translucent cover 131. The optical fiber bundle 132 is an aggregate of optical fibers 132a corresponding to respective pixels of the display panel 106 in a one-to-one relationship. In FIG. 3, for the sake of explanation, the optical fibers 132a are shown as if they are floating from the surface of the display panel 106. However, one end of each of the optical fibers 132a is bonded to the surface of the display panel 106 by a light-guiding type adhesive. An outer circumferential surface of the aggregate of the optical fibers 132a is covered and tied with a coating 132b. In this way, the translucent cover 131, the optical fiber bundle 132 and the display panel 106 are connected to one another and integrated.

A luminous flux of the display right-eye image 191a displayed on the display panel 106 enters from one of the ends of the optical fibers 132a and exits from the other end of the optical fibers 132a. An aggregate of the other ends of the optical fibers 132a is a light emission surface of the optical fibers 132a and forms a virtual screen extending along the inner curved surface of the translucent cover 131. Accordingly, the display right-eye image 191a displayed on the display panel 106 is projected onto the virtual screen and is converted into a projected right-eye image 192a observed by the user.

Since the display right-eye image 191a displayed as a planar surface is converted into the projected right-eye image 192a projected as a curved surface, the eye control part 105 may adjust in advance a shape of the display right-eye image 191a to be displayed so that the projected right-eye image 192a to be observed has a correct shape. In this case, for example, even for a pattern of a single black part of the eye, the eye control part 208 adjusts a position and the shape of the display right-eye image 191a to be displayed, depending on the projected position of the projected right-eye image 192a on the virtual screen.

Figure 4:
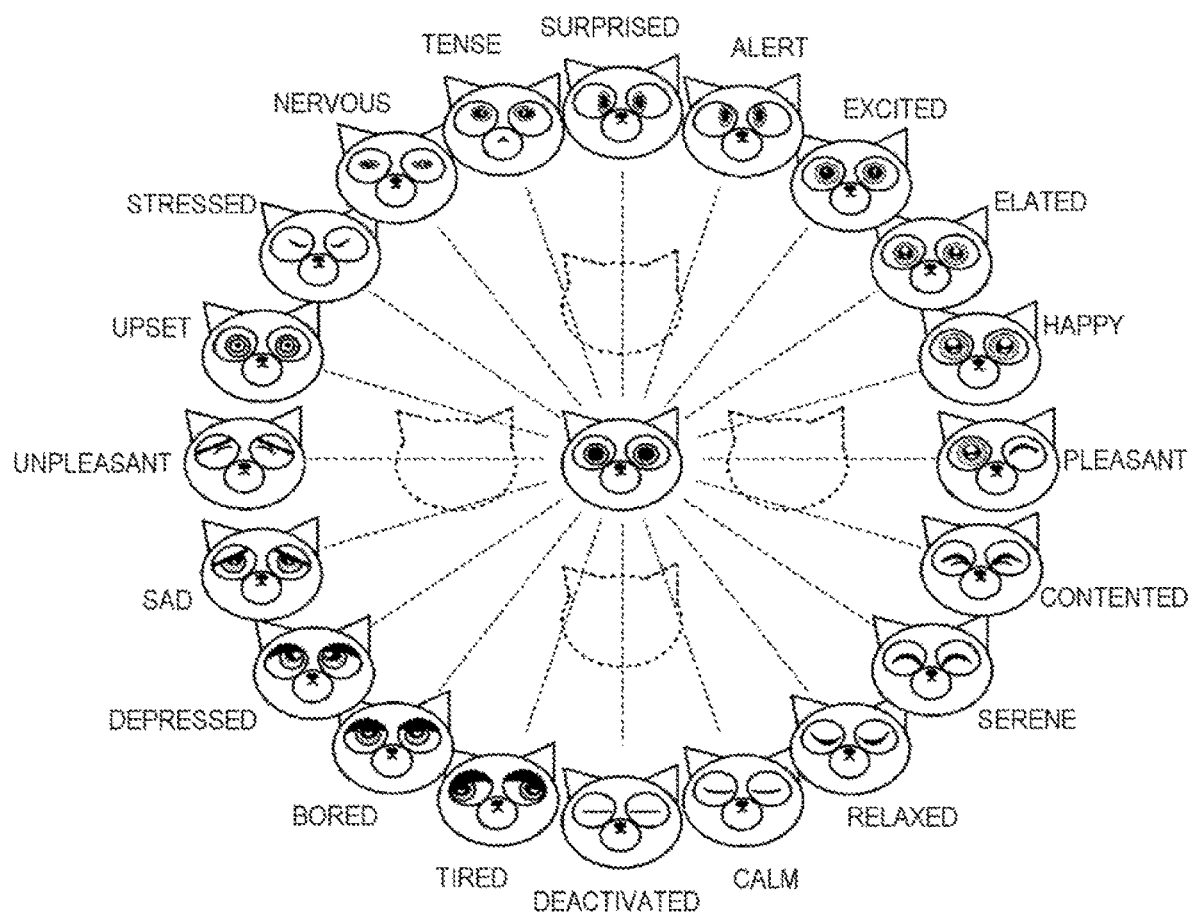
FIG. 4 is a diagram showing a relationship between facial expressions of the robot and a Russell's circumplex model.

FIG. 4 is a diagram showing a relationship between facial expressions expressed by the robot 100 and a Russell's circumplex model. In FIG. 4, shapes of the face portion 120 are arranged side by side. However, the robot 100 according to the present embodiment is configured to control a user's impression received from the entire face portion 120 by changing a right eye image and a left eye image displayed on the display panel 106. Therefore, the image data stored in the response expression DB 320 in association with types and degrees of emotions described below is a set of image data corresponding to the right eye image and the left eye image.

The Russell's circumplex model, which has been proposed in the field of psychology, is a model in which all emotions are annularly arranged in a plane having axes of "pleasant-unpleasant" and "surprised-deactivated." There are various opinions as to which positions concrete emotions can be arranged. In the present embodiment, as shown in FIG. 4, twenty types of emotions including "alert," "excited," "elated," "happy," "pleasant," "contented," "serene," "relaxed," "calm," "deactivated," "tired," "bored," "depressed," "sad," "unpleasant," "upset," "stressed," "nervous," and "tense" are evenly arranged clockwise from the "surprised" on a circumference. Therefore, a type of each emotion is defined along a radial direction around "expressionless" as a center, and a distance from the center indicates a degree of each emotion. FIG. 4 shows facial expressions that represent states when the emotions are most strongly expressed. In addition, intermediate facial expressions corresponding to the degrees of the emotions are arranged on the radial lines indicated by dotted lines.

In the Russell's circumplex model illustrated in FIG. 4, emotions adjacent to each other are similar emotions. Therefore, the expressions of the adjacent emotions are also similar to each other. Patterns of image data associated with the types and degrees of the respective emotions are created in advance with the above-described relationship.

Figure 5:
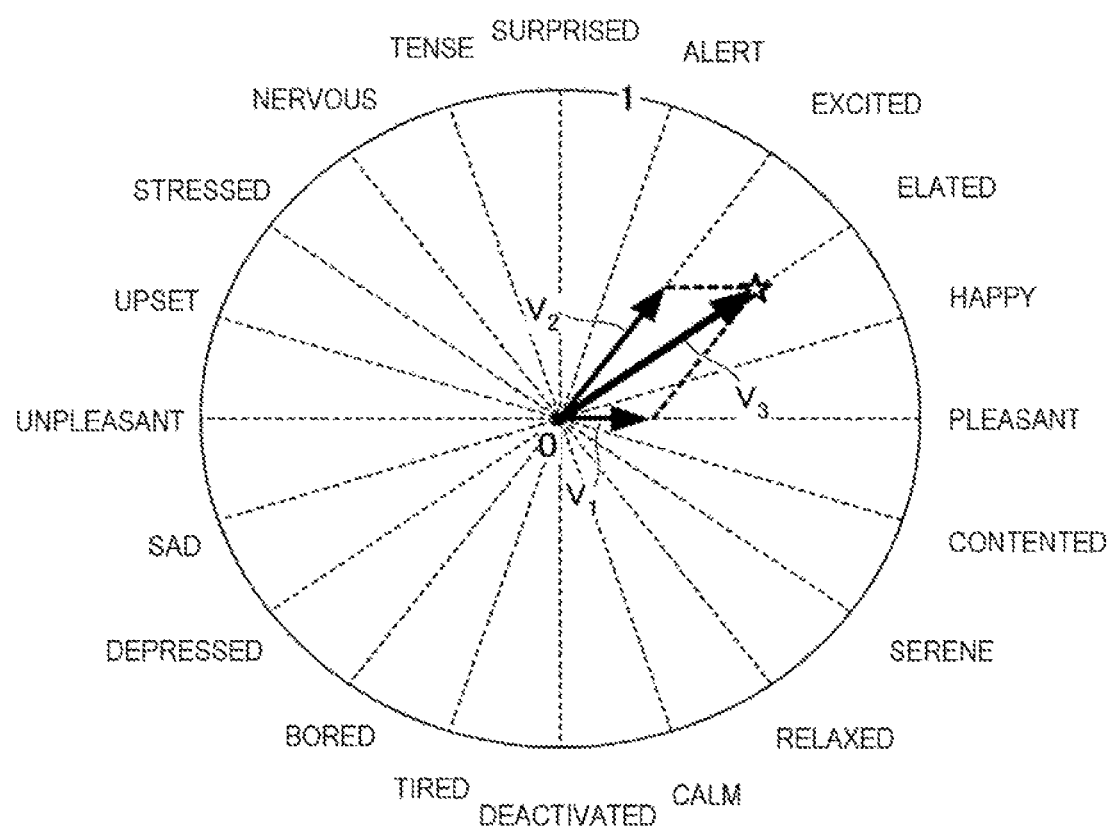
FIG. 5 is an explanatory diagram concerning an empathic emotion determination method.

Next, a method leading to determination of an empathic emotion will be described. FIG. 5 is an explanatory diagram concerning an empathic emotion determination method and shows a toroidal coordinate system obtained by removing the appearances of the face portion 120 from the Russell's circumplex model of FIG. 4. The center of the circle representing "expressionless" is set to "0," and a maximum value of each emotion is set to "1." That is to say, the Russell's circumplex model is represented by a circle with a radius of one.

A type and degree of the emotion (first emotion) estimated from the utterance of the user by the first emotion estimation part 203 are represented by a vector $V_1$. In the illustrated example, the vector $V_1$ has a length of about 0.25 in the "pleasant" direction. Furthermore, a type and degree of the emotion (second emotion) estimated from the utterance of the user by the second emotion estimation part 204 are represented by a vector $V_2$. In the illustrated example, the vector $V_2$ has a length of about 0.5 in the "excited" direction.

The empathic emotion determination part 205 calculates a vector $V_3$ representing an empathic emotion by obtaining a sum of the vector $V_1$ and the vector $V_2$ on the Russell's circumplex model. In the illustrated example, the vector $V_3$ has a length of about 0.67 in the "elated" direction. Therefore, the empathic emotion determination part 205 determines the type of the empathic emotion="elated" and the degree of the empathic emotion=0.67, which are represented by the coordinates of a pentagram in FIG. 5.

Figure 6:
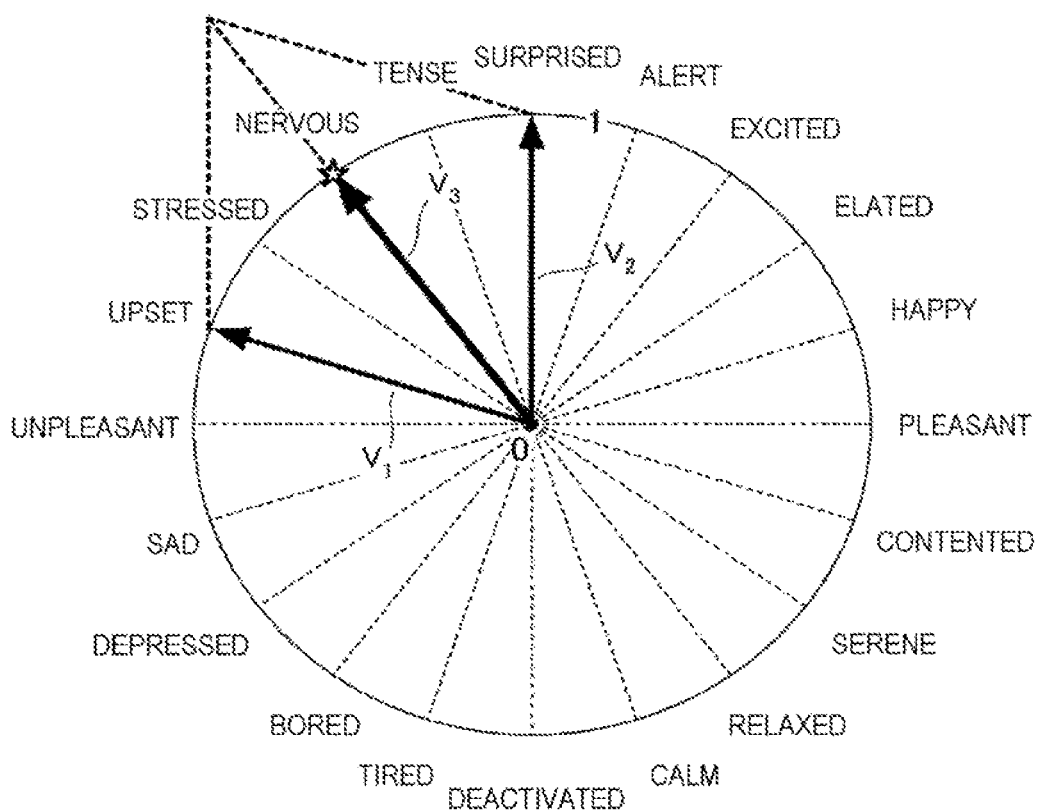
FIG. 6 is an explanatory diagram concerning an empathic emotion determination method of another example.

FIG. 6 is an explanatory diagram concerning an empathic emotion determination method of another example. FIG. 6 also shows the same toroidal coordinate system as that in FIG. 5.

It is assumed that the first emotion estimation part 203 estimates the type of the first emotion="upset" and the degree of the first emotion=1, as represented by a vector $V_1$, and the second emotion estimation part 204 estimates the type of the second emotion="surprised" and the degree of the second emotion=1, as represented by a vector $V_2$. In this case, when a sum of the vector $V_1$ and the vector $V_2$ is calculated, the direction of the sum is "nervous", but the magnitude of the sum exceeds one. Thus, the empathic emotion determination part 205 determines a vector $V_3$ as the type of the empathic emotion="nervous" and the degree of the empathic emotion=1, which are represented by the coordinates of a pentagram in FIG. 6.

In the above-described manner, by providing an exception rule in which the magnitude of the vector $V_3$ is set to one when it exceeds one, even if the vector $V_1$ and the vector $V_2$ have any orientation and any magnitude, it is possible to determine the type and degree of the empathic emotion.

In the present embodiment, each of the first emotion estimation part 203 and the second emotion estimation part 204 is configured to estimate the type of emotion together with the degree of emotion. However, even with a configuration in which the degree of emotion is not estimated, it is possible to determine the type of the empathic emotion by the method according to the present embodiment. Specifically, if the type of the first emotion is estimated to be "upset" and the type of the second emotion is estimated to be "surprised", vector calculation may be performed under the assumption that the degree of each of the first emotion and the second emotion is a fixed value "1." As a result, the "nervous" that is the type of emotion corresponding to the direction of the calculated vector may be determined as the type of the empathic emotion.

Figure 7:
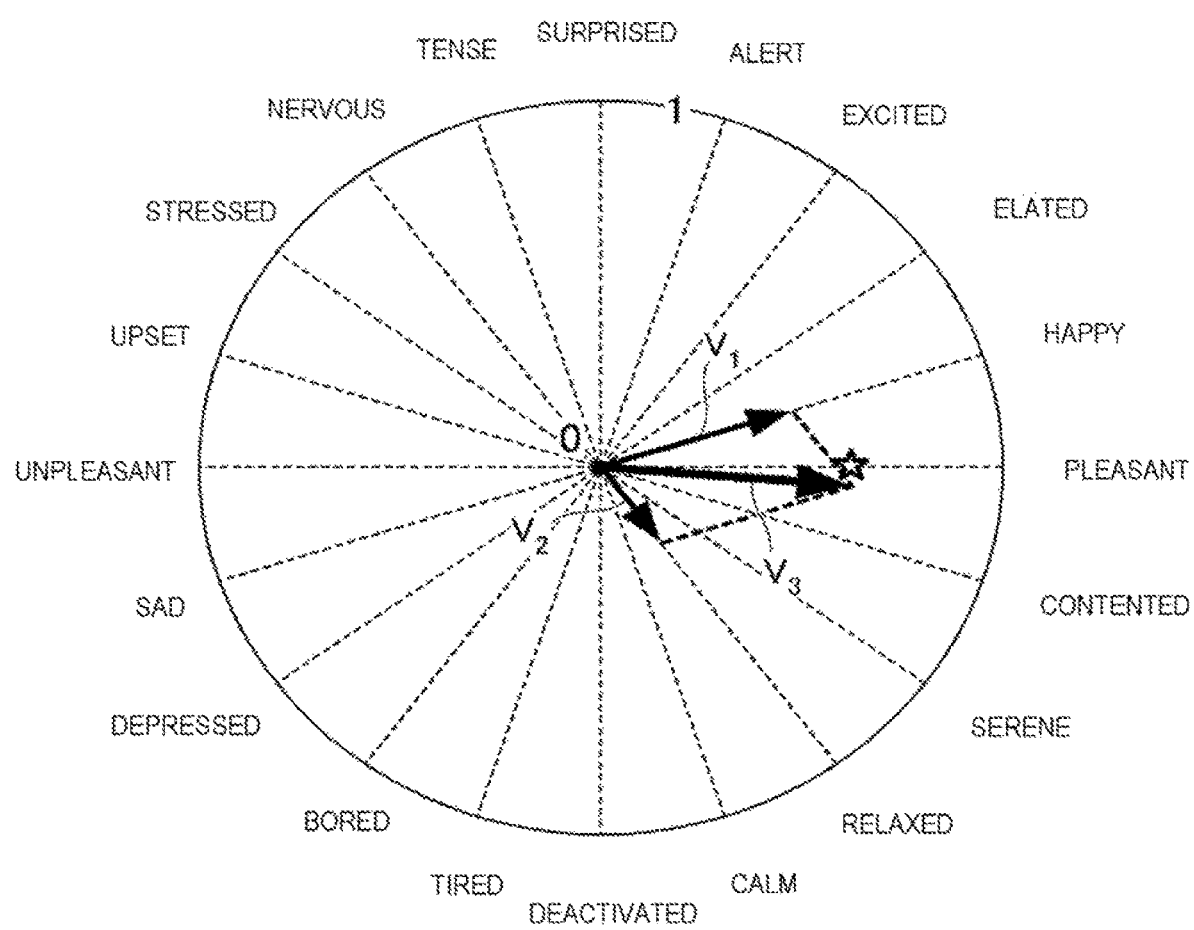
FIG. 7 is an explanatory diagram concerning an empathic emotion determination method of a further example.

FIG. 7 is an explanatory diagram concerning an empathic emotion determination method of a further example. FIG. 7 also shows the same toroidal coordinate system as that in FIG. 5.

It is assumed that the first emotion estimation part 203 estimates the type of the first emotion="happy" and the degree of the first emotion=0.50, as represented by a vector $V_1$, and the second emotion estimation part 204 estimates the type of the second emotion="relaxed" and the degree of the second emotion=0.25, as represented by a vector $V_2$. In this case, when a sum of the vector $V_1$ and the vector $V_2$ is calculated, a vector $V_3$ has a length of about 0.62 in the direction between "pleasant" and "contented." When the direction of the calculated vector $V_3$ is between two emotions as described above, image data corresponding to tip coordinates of the vector $V_3$ is not stored in the response expression DB 320. Thus, the empathic emotion determination part 205 draws a perpendicular line down to one of the radial lines of the two emotions whichever is nearer, and determines a foot of the perpendicular line as coordinates of empathic emotion. In the example of FIG. 7, the coordinates of a pentagram shown on the radial line of "pleasant" are the coordinates of empathic emotion. That is to say, the empathic emotion determination part 205 determines the type of the empathic emotion="pleasant" and the degree of the empathic emotion=0.61. As described above, the empathic emotion determination part 205 can uniquely determine the type and degree of the empathic emotion even if the direction of the vector $V_3$ does not extend along the radial line of any emotion.

The method of determining the type and degree of the empathic emotion described with reference to FIGS. 5 to 7 is a method capable of being applied to a case where the second emotion estimation part 204 estimates the type and degree of the second emotion, that is to say, a case where the vector $V_2$ can be calculated. In a case where the second emotion estimation part 204 fails to estimate the second emotion, the type and degree of the empathic emotion may be determined by setting $V_3=V_1$.

When the subject emotion determined by the subject emotion determination part 206 is not taken into account, the expression selection part 207 acquires, from the response expression DB 320, image data of eye expression corresponding to the coordinates of the empathic emotion determined by the empathic emotion determination part 205 in the Russell's circumplex model. Upon acquiring the image data, the expression selection part 207 delivers the image data to the eye control part 208, and the eye control part 208 converts the received image data into an image signal and displays the image signal on the display panel 106. Thus, the facial expression corresponding to the type and degree of the determined empathic emotion is created on the face portion 120. Alternatively, when the subject emotion determined by the subject emotion determination part 206 is combined with the empathic emotion determined by the empathic emotion determination part 205, vector calculation is first performed on the vector of empathic emotion and the vector of subject emotion.

Figure 8:
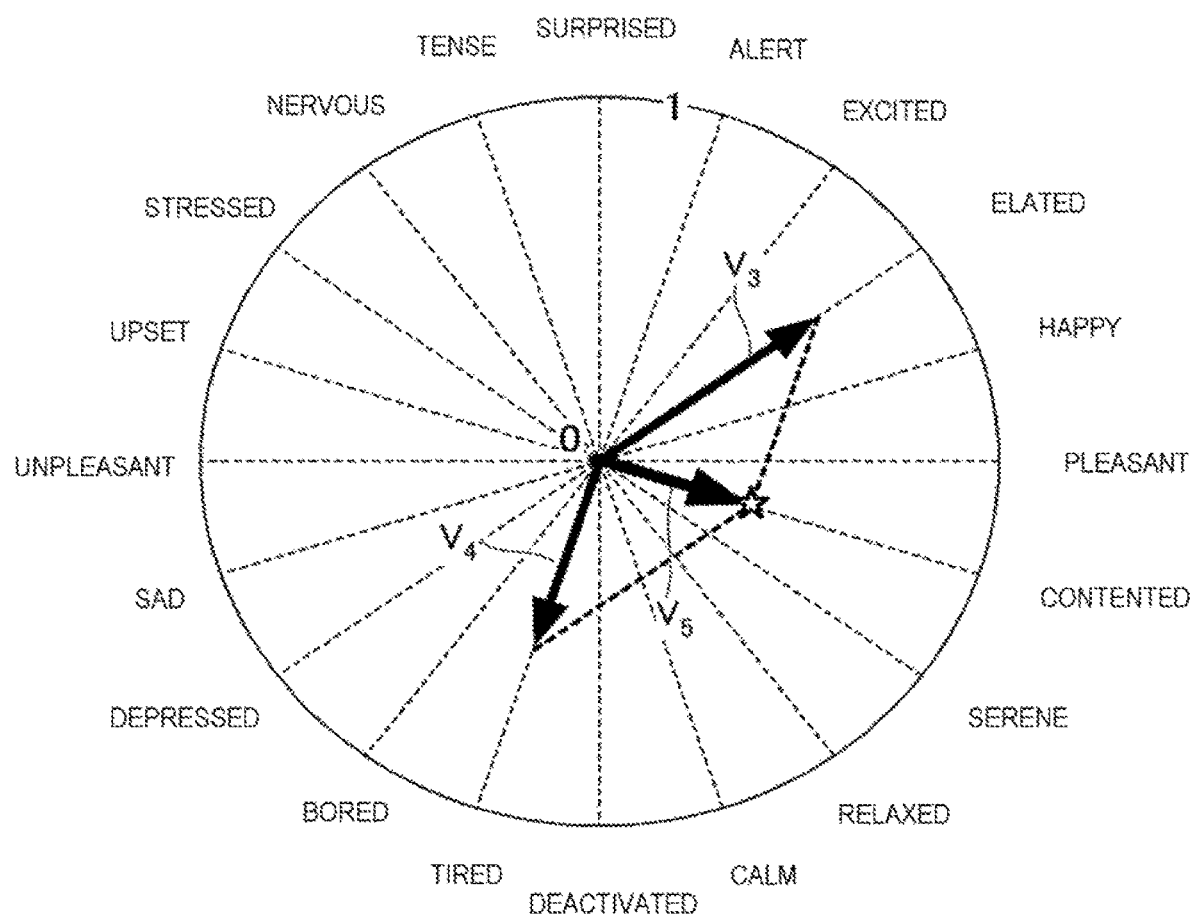
FIG. 8 is an explanatory diagram concerning an empathic emotion determination method in a case of combining subject emotions.

FIG. 8 is an explanatory diagram concerning a method of determining a combined emotion expressed by the face portion 120 when combining subject emotions. FIG. 8 also shows the same toroidal coordinate system as that in FIG. 5. It is assumed that the vector $V_3$ calculated by the empathic emotion determination part 205 has a length of about 0.67 in the direction of "elated" as in the example of FIG. 5.

As described above, the subject emotion is a certain emotion that is associated, in a pseudo manner, with a parameter indicating a state of the robot 100. In the present embodiment, the remaining capacity of the battery 111 is associated with "tired." That is to say, when the robot 100 expresses only the subject emotion, the robot 100 expresses the more bored facial expression as the remaining capacity of the battery 111 decreases. Specifically, the subject emotion is represented by a vector $V_4$ extending along a radial line of "tired," and the remaining capacity is made to correspond to a length of the vector $V_4$. For example, when the detection signal received from the battery monitoring part 112 indicates the remaining capacity=100%, the length of the vector $V_4$ is set to "0." When the detection signal indicates the remaining capacity=50%, the length of the vector $V_4$ is set to "0.5." When the detection signal indicates the remaining capacity=0%, the length of the vector $V_4$ is set to "1." In the example of FIG. 8, the subject emotion determination part 206 determines the vector $V_4$ as the type of the subject emotion="tired" and the degree of the subject emotion=0.5.

Similar to the above-described empathic emotion determination part 205, the expression selection part 207 calculates a vector $V_5$ representing a combined emotion by obtaining a sum of the vector $V_3$ and the vector $V_4$. In the example of FIG. 8, the vector $V_5$ has a length of about 0.40 in the direction of "contented". Therefore, the expression selection part 207 determines the type of the combined emotion="contented" and the degree of the combined emotion=0.40, which are represented by the coordinates of a pentagram in FIG. 8.

In the calculation of the sum of the vector $V_3$ and the vector $V_4$, when the vector $V_5$ exceeds one, the expression selection part 207 deals with the situation as described with reference to FIG. 6. In addition, when the vector $V_5$ is not positioned on a radial line indicating a specific emotion, the expression selection part 207 deals with the situation as described with reference to FIG. 7. In the present embodiment, the parameter associated with the subject emotion is described as being limited to the remaining capacity of the battery 111. However, other parameters may be associated with different emotions. For example, when the number of times of dialogue performed in the past with a specific user is recorded, the number of times of dialogue may be associated with "elated" as a parameter. By way of this association, when the number of times of dialogue with the user increases, the robot 100 strongly expresses the facial expression of "elated" as a subject emotion as if the robot 100 is delighted to be able to talk again. When a plurality of parameters indicating states of the robot 100 is associated with different emotions, the subject emotion determination part 206 calculates a sum of vectors of emotions and determines a type and degree of one subject emotion, in the same manner as the empathic emotion determination part 205 does.

Upon determining the type and degree of the combined emotion by calculating the vector $V_5$, the expression selection part 207 acquires, from the response expression DB 320, image data of an eye expression corresponding to the determined coordinates in the Russell's circumplex model. Upon acquiring the image data, the expression selection part 207 delivers the image data to the eye control part 208. The eye control part 208 converts the received image data into an image signal and displays the image signal on the display panel 106. Thus, a facial expression corresponding to the type and degree of the combined emotion thus determined is created on the face portion 120.

When preset conditions are satisfied, the expression selection part 207 may acquire, from the response expression DB 320, the image data of the eye expression corresponding to the type and degree of the subject emotion without being combined with the empathic emotion. For example, when the robot 100 determines that there is no nearby user to make dialogue with, the robot 100 may express the facial expression of "tired," so that it possible to appeal to the surroundings that the remaining capacity of the battery 111 is small. In the dialogue with the user, when the user asks a question about the state of the robot 100, the robot 100 may more directly notify the user of the state of the robot 100.

Figure 9:
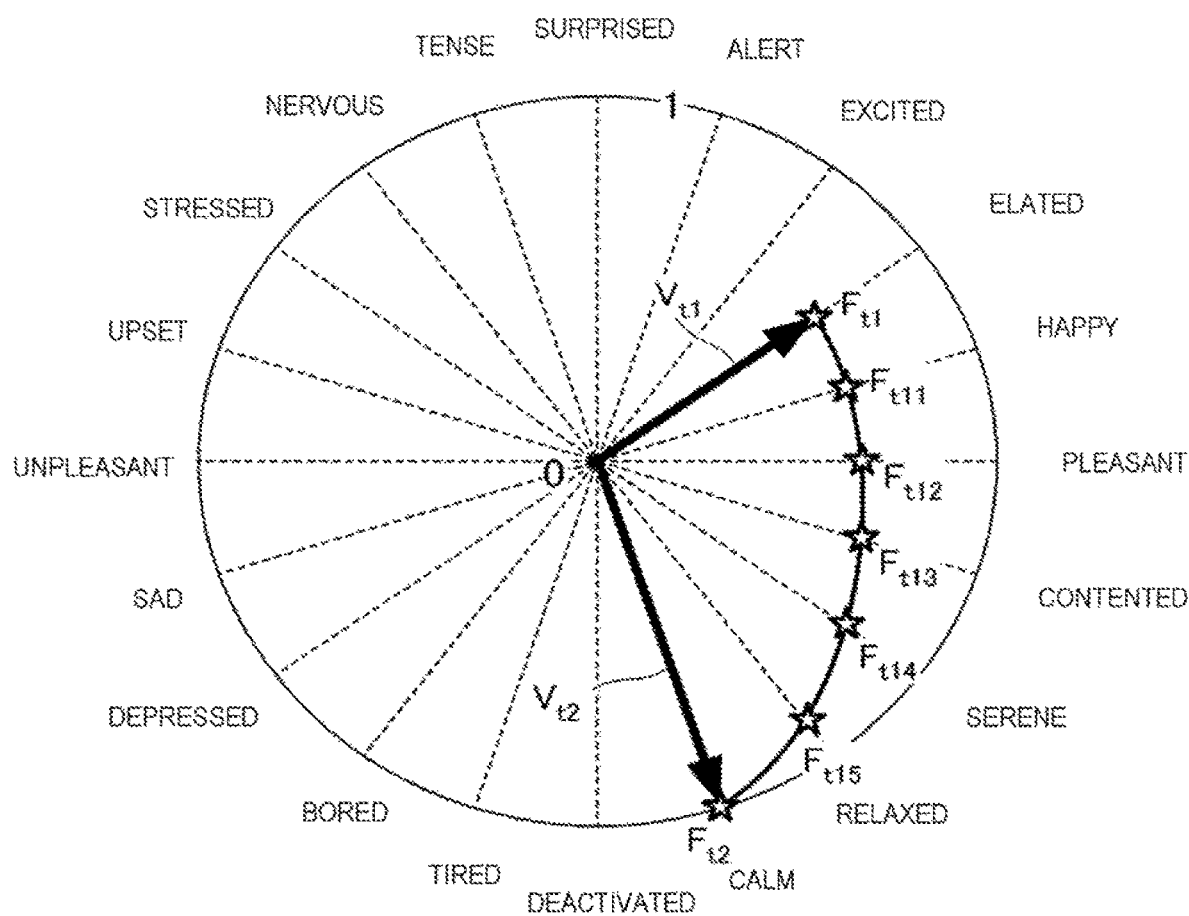
FIG. 9 is a diagram for explaining a transition of display accompanying a change of emotion.

Next, a process performed when an emotion changes sequentially as a dialogue with a user progresses will be described. FIG. 9 is a diagram for explaining a transition of display accompanying a change of emotion. FIG. 9 also shows the same toroidal coordinate system as that in FIG. 5.

In a time period in which a conversation with a user continues, it is assumed that as a result of the above-described vector calculation, the expression selection part 207 obtains a vector $V_{t1}$ as the type and degree of the emotion expressed at time $t_1$. The coordinates $F_{t1}$ indicated by the vector $V_{t1}$ are the type of the emotion="elated" and the degree of the emotion=0.67. Subsequently, it is assumed that a vector $V_{t2}$ is obtained as the type and degree of the emotion expressed at time $t_2$. The coordinates $F_{t2}$ indicated by the vector $V_{t2}$ are the type of the emotion="calm" and the degree of the emotion=1. When emotions expressed at consecutive times are significantly different as described above, the facial expression of the face portion 120 may be suddenly and greatly changed, and the user may sometimes feel uncomfortable.

Thus, in the present embodiment, the coordinates $F_{t1}$ and the coordinates $F_{t2}$ are smoothly connected by a curve, and interpolation coordinates are set at points where the curve intersects the radial lines of the respective emotions. In the example of FIG. 9, six different types of emotions (from "elated" to "calm") exist from the coordinates $F_{t1}$ to the coordinates $F_{t2}$, and a change in degree of emotion is 1−0.67=0.33. Thus, the interpolation coordinates may be set so that the degree of emotion increases by 0.33/6=0.055 each time when a transition from one emotion to its adjacent emotion is made. In this way, coordinates $F_{t11}$, coordinates $F_{t12}$, coordinates $F_{t13}$, coordinates $F_{t14}$, and coordinates $F_{t15}$ are set at the points where the curve intersects the respective radial lines of "happy," "pleasant," "content," "serene," and "relaxed." Then, the expression selection part 207 delivers image data corresponding to the coordinates $F_{t1}$ to the eye control part 208. Thereafter, the expression selection part 207 successively delivers image data corresponding to the coordinates $F_{t11}$, $F_{t12}$, $F_{t13}$, $F_{t14}$, and $F_{t15}$ to the eye control part 208 before image data corresponding to the coordinates $F_{t2}$ is delivered to the eye control part 208. The eye control part 208 converts the image data corresponding to the coordinate $F_{t1}$ into an image signal at time $t_1$ and displays the image signal on the display panel 106. Thereafter, until the time $t_2$, the eye control part 208 successively converts the image data corresponding to the coordinates $F_{t1}$, $F_{t12}$, $F_{t13}$, $F_{t14}$, and $F_{t15}$ into image signals and displays the image signals on the display panel 106. Then, at time $t_2$, the image data corresponding to the coordinates $Ft_2$ is converted into an image signal and displayed on the display panel 106. In this manner, by inserting facial expressions that interpolates between the facial expression expressed at time $t_1$ and the facial expression expressed at time $t_2$ that is continuous with time $t_1$, the user may get an impression that the change of the face portion 120 is smooth and continuous. The number of facial expressions to be interpolated may change according to conditions, such as a time period between time $t_1$ and time $t_2$, a proximity between the coordinates $F_{t1}$ and the coordinates $F_{t2}$, and the like.

On the other hand, when emotions expressed at consecutive times do not change at all, the facial expression of the face portion 120 does not change. In this case as well, the user may feel discomfort. Thus, the empathic emotion determination part 205 may change the calculated vector $V_3$ to a vector $V_3'$ that is approximated within a predetermined range and may output the vector $V_3'$. For example, with respect to the emotion represented by the calculated vector $V_3$, the range up to an adjacent emotion on the Russell's circumplex model is assumed to be the predetermined range. In this way, if fluctuation is given to the output of the empathic emotion, the user may enjoy a more varied expression.

Figure 10:
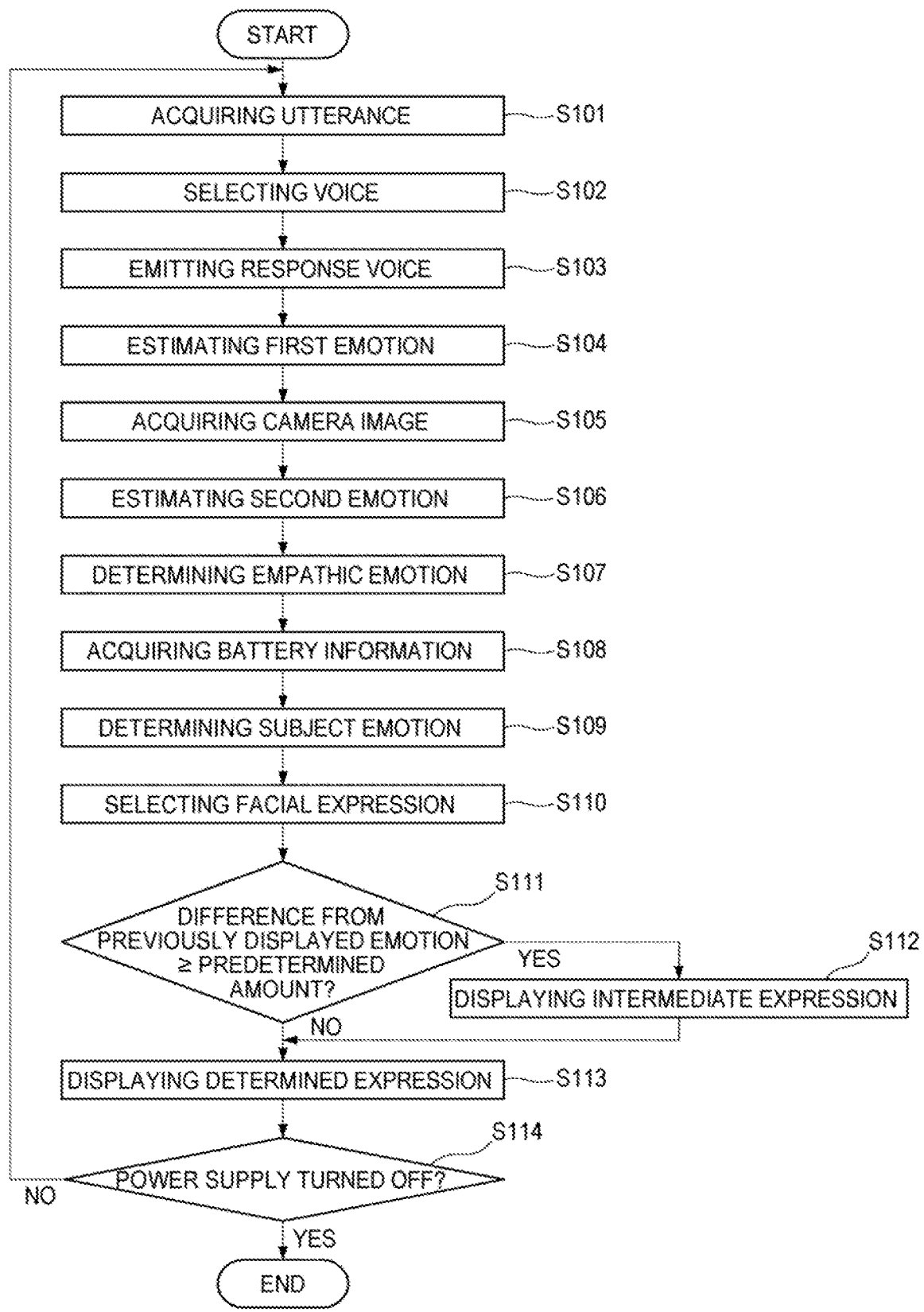
FIG. 10 is a flowchart showing a procedure of an operation process.

Next, a procedure of an operation process executed by the control part 200 will be described. FIG. 10 is a flowchart showing the procedure of the operation process. The flow is started when a power supply of the robot 100 is turned on.

In step S101, the utterance recognition part 201 acquires a user's utterance talking to the robot 100 via the microphone 101. The flow proceeds to step S102. The voice selection part 209 selects a sentence suitable for a conversation with respect to the acquired utterance content of the user, collects utterance data corresponding to the selected sentence from the response voice DB 310, and delivers the utterance data to the utterance control part 210. The flow proceeds to step S103. The utterance control part 210 converts the received utterance data into a voice signal and causes the voice signal to be uttered as a voice from the speaker 109. In step S104, the first emotion estimation part 203 estimates a type and degree of a user's first emotion from the utterance of the user.

In step S105, the expression recognition part 202 acquires from the camera 102 a camera image that captures a facial expression of the user who talks to the robot 100. The flow proceeds to step S106. The second emotion estimation part 204 estimates a type and degree of a user's second emotion using an expression feature amount received from the expression recognition part 202.

In step S107, the empathic emotion determination part 205 determines the type and degree of the empathic emotion by calculating the sum of the vector $V_1$ representing the type and degree of the first emotion and the vector $V_2$ representing the type and degree of the second emotion. When the second emotion estimation part 204 fails to estimate the type and degree of the second emotion in step S106, the empathic emotion determination part 205 determines the type and degree of the first emotion as the type and degree of the empathic emotion.

In step S108, the subject emotion determination part 206 acquires a detection signal indicating a remaining capacity of the battery 111 from the battery monitoring part 112. In step S109, the subject emotion determination part 206 converts a level of the detection signal into a type and degree of an associated subject emotion of the robot 100. The expression selection part 207 calculates a type and degree of a combined emotion from the received types and degrees of the empathic emotion and the subject emotion, and acquires image data of a facial expression corresponding to the calculation result from the response expression DB 320.

The flow proceeds to step S111. The expression selection part 207 determines whether or not the difference between the combined emotion corresponding to the previously acquired image data and the combined emotion corresponding to the currently acquired image data is equal to or larger than a predetermined difference. The predetermined difference is, for example, three emotions arranged along the circumference of the Russell's circumplex model. In this case, if the current combined emotion is spaced apart by three or more emotions in the circumferential direction from the previous combined emotion, the flow proceeds to YES (step S112). If the current combined emotion is spaced apart by two or less emotions in the circumferential direction from the previous combined emotion, the flow proceeds to NO (step S113).

In the case of proceeding to step S112, the expression selection part 207 sets intermediate emotions interpolating between the previous combined emotion and the current combined emotion, and acquires image data corresponding to the intermediate emotions from the response expression DB 320. Then, the eye control part 208 converts the image data into image signals and sequentially displays the image signals on the display panel 106. After the images corresponding to the intermediate emotions have been displayed, the flow proceeds to step S113.

In step S113, the expression selection part 207 delivers the image data acquired by the process of step S110 to the eye control part 208. The eye control part 208 converts the image data into an image signal and displays the image signal on the display panel 106. Then, the flow proceeds to step S114. The control part 200 determines whether or not the power supply of the robot 100 is turned off. If the power supply is not turned off, the flow returns to step S101 where the communication with the user is repeated. If the power supply is turned off, a series of processes is ended.

Timings of the response utterance in step S103 and the display of the determined expression in step S113 may be adjusted so as to be optimal with each other. In addition, the process related to the user's utterance, the process related to the user's facial expression, and the process related to the battery need not be performed in the order described above, and may be performed in parallel.

The robot 100 described above is a communication device as a character that performs a dialogue with a user. The robot 100 selects and generates a response expression using the first emotion estimated from the utterance of the user and the second emotion estimated from the user's face image information as information not uttered by the user. The response expression selected and generated in the case of using the second emotion may differ from the response expression selected and generated in the case of not using the second emotion. Therefore, even if the user's utterances are the same, the facial expression expressed by the face portion 120 of the robot 100 is rich in variation. Thus, it can be expected that the user has increased attachment to the robot 100 without getting tired of the dialogue.

Since the expressions of the face portion 120 are created in consideration of not only the user's utterance but also information other than the utterance, even if the utterances of the user are the same, the combinations of the response voice emitted by the robot 100 and the response expression of the face portion 120 are varied. Therefore, the user may enjoy unexpected reactions from the robot 100. Eventually, it can be expected to increase user's sense of affinity for the robot 100.

Figure 11:
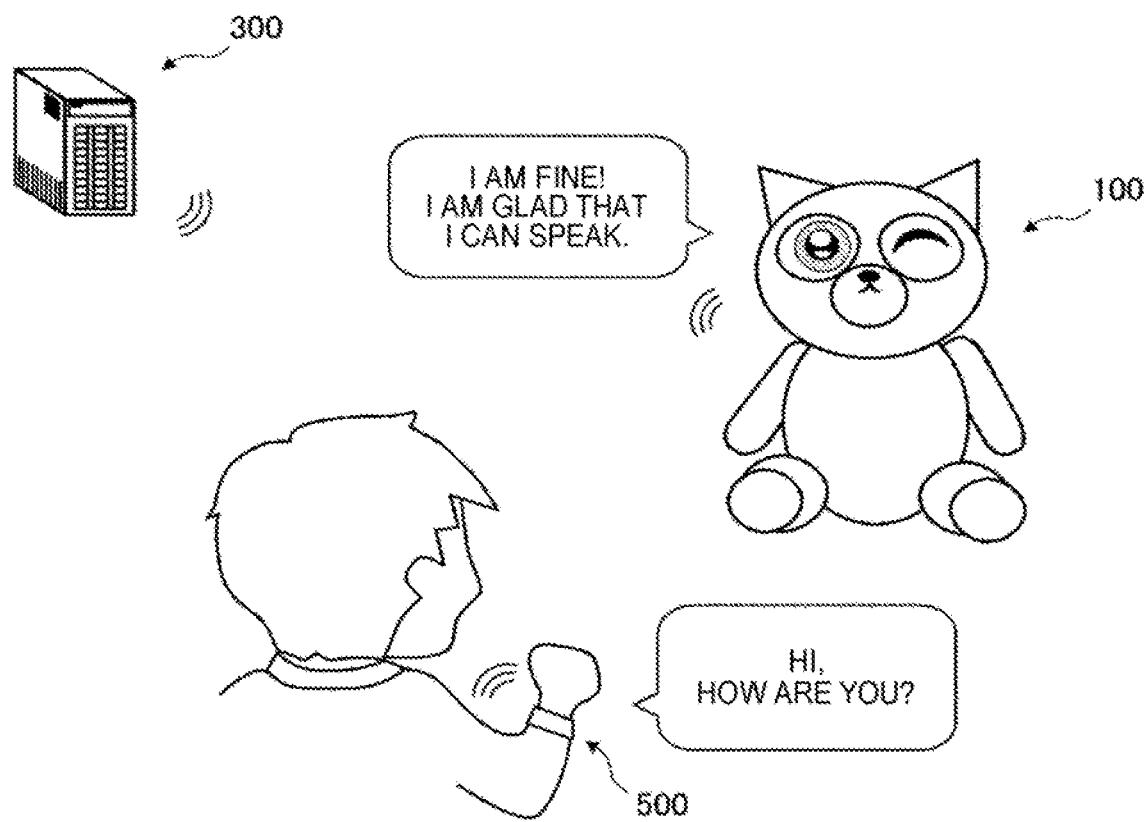
FIG. 11 is a schematic diagram of a communication system according to a second embodiment.

Next, a second embodiment will be described. FIG. 11 is a schematic diagram of a communication system according to a second embodiment. In the first embodiment, all the main functional elements are provided in a main body of the robot 100 so that the robot 100 can independently communicate with a user. However, a robot 100' according to the second embodiment adopts a configuration in which functional elements related to calculation is left to a server 300.

For example, when a user speaks "Hi, How are you?" to the robot 100', a microphone of the robot 100' captures a voice of the user. The robot 100' converts the captured voice into a voice signal and transmits the voice signal to the server 300 by wireless communication. Furthermore, a camera incorporated in the robot 100' captures an image of a face of the user. The robot 100' converts an output signal of the camera into an image signal and transmits the image signal to the server 300 by wireless communication. Using these pieces of information, the server 300 selects voice data of a response voice (in the illustrated example "I am fine! I am glad that I can speak") and image data of a response expression (in the illustrated example, the expression of "pleasant"), and transmits the selected data to the robot 100'. The robot 100' emits from the speaker a voice corresponding to the received voice data and displays a pattern corresponding to the received image data.

In the present embodiment, a wrist sensor 500 that can be additionally adopted to acquire biological information of the user will also be described. The user wears the wrist sensor 500 by wrapping it around an arm of the user. The wrist sensor 500 detects, for example, the user's pulse and perspiration state, and transmits the detection result to the server 300.

Figure 12:
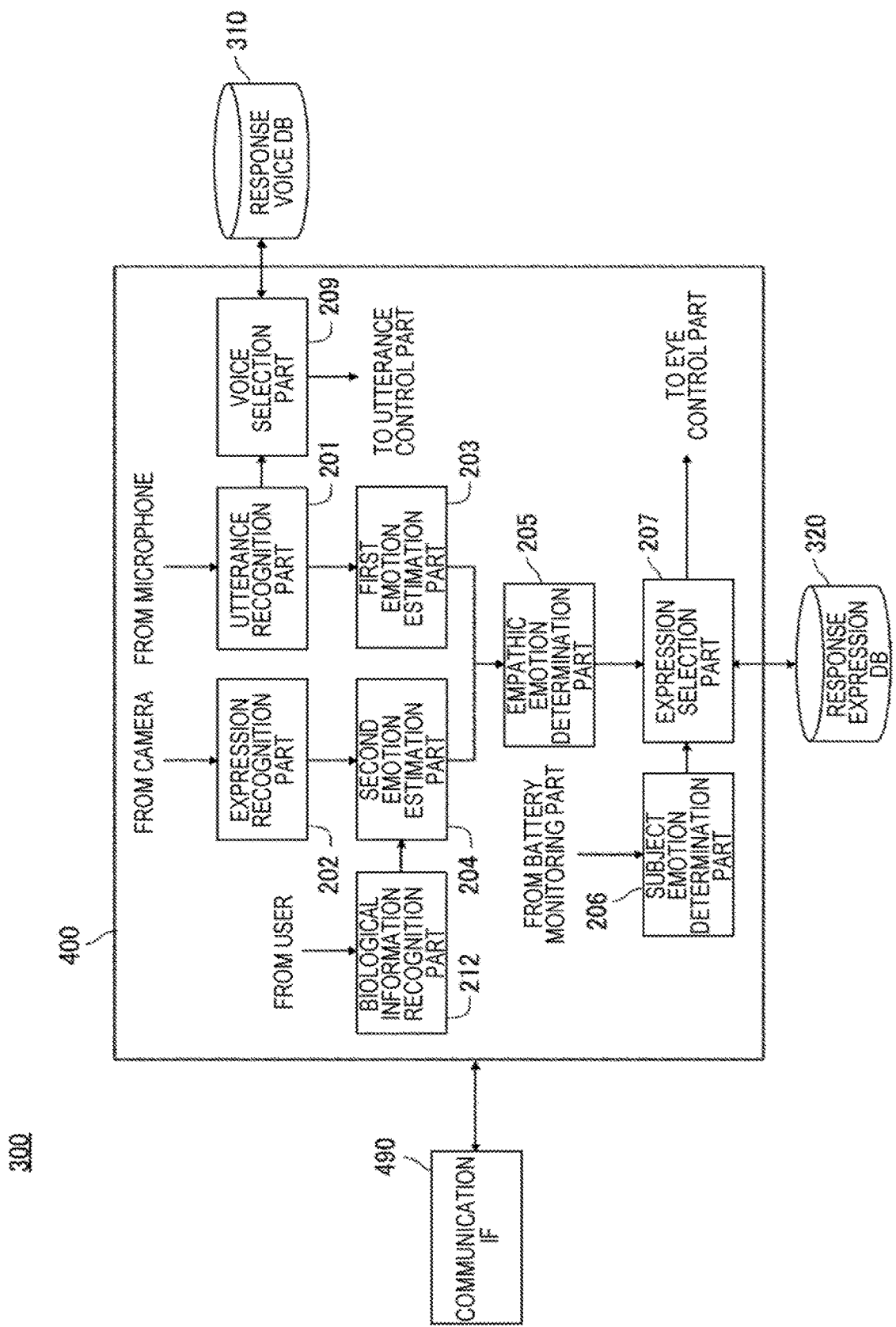
FIG. 12 is a system configuration diagram of a server.

FIG. 12 is a system configuration diagram of the server 300. The same names are assigned to the elements that basically have the same functions as the elements described in the first embodiment. Explanations of the functions of the elements are omitted unless otherwise specifically mentioned. In the present embodiment, the server 300 functions as the entire communication device that performs various calculations and the like.

The server 300 mainly includes an arithmetic processing part 400, a communication IF 490, the response voice DB 310, and the response expression DB 320. The arithmetic processing part 400 is, for example, a CPU, and operates as a part for executing the respective functions of the utterance recognition part 201, the expression recognition part 202, the first emotion estimation part 203, the second emotion estimation part 204, the empathic emotion determination part 205, the subject emotion determination part 206, and the expression selection part 207. The arithmetic processing part 400 also operates as a biological information recognition part 212 as a function execution part.

The communication IF 490 is a communication interface for exchanging control signals and data with the robot 100', and is, for example, a wireless LAN unit. The response voice DB 310 has the same configuration as the response voice DB 310 described in the first embodiment, and is connected to the voice selection part 209. Furthermore, the response expression DB 320 has the same configuration as the response expression DB 320 described in the first embodiment, and is connected to the expression selection part 207.

The utterance recognition part 201 receives a voice signal from the robot 100' via the communication IF 490. The utterance recognition part 201 functions as an utterance acquisition part that, in cooperation with the communication IF 490, acquires a utterance of a user talking to the robot 100. Furthermore, the expression recognition part 202 receives an image signal from the robot 100' via the communication IF 490. The expression recognition part 202 functions as an information acquisition part that, in cooperation with the communication IF 490, acquires a facial expression of a user as information different from the utterance of the user.

The biological information recognition part 212 acquires a biological signal indicating biological information of the user from the wrist sensor 500 via the communication IF 490. Then, in accordance with analysis targets, such as pulse, perspiration, and the like, the biological information recognition part 212 extracts a characteristic signal from the acquired biological signal and delivers the characteristic signal to the second emotion estimation part 204. The biological information recognition part 212 functions as an information acquisition part that, in cooperation with the communication IF 490, acquires the biological information of the user as information different from the utterance of the user.

The second emotion estimation part 204 combines the emotion estimated from the facial expression of the user and the emotion estimated from the biological information to determine a type and degree of a second emotion. Specifically, similar to the method described with reference to FIGS. 5 to 7, the second emotion estimation part 204 determines the vector $V_2$ of the second emotion by representing the respective emotions as vectors and calculating the sum of the vectors.

The expression selection part 207 transmits the image data acquired from the response expression DB 320 to the robot 100' via the communication IF 490. Similarly, the voice selection part 209 transmits the utterance data corresponding to the selected sentence to the robot 100' via the communication IF 490.

Figure 13:
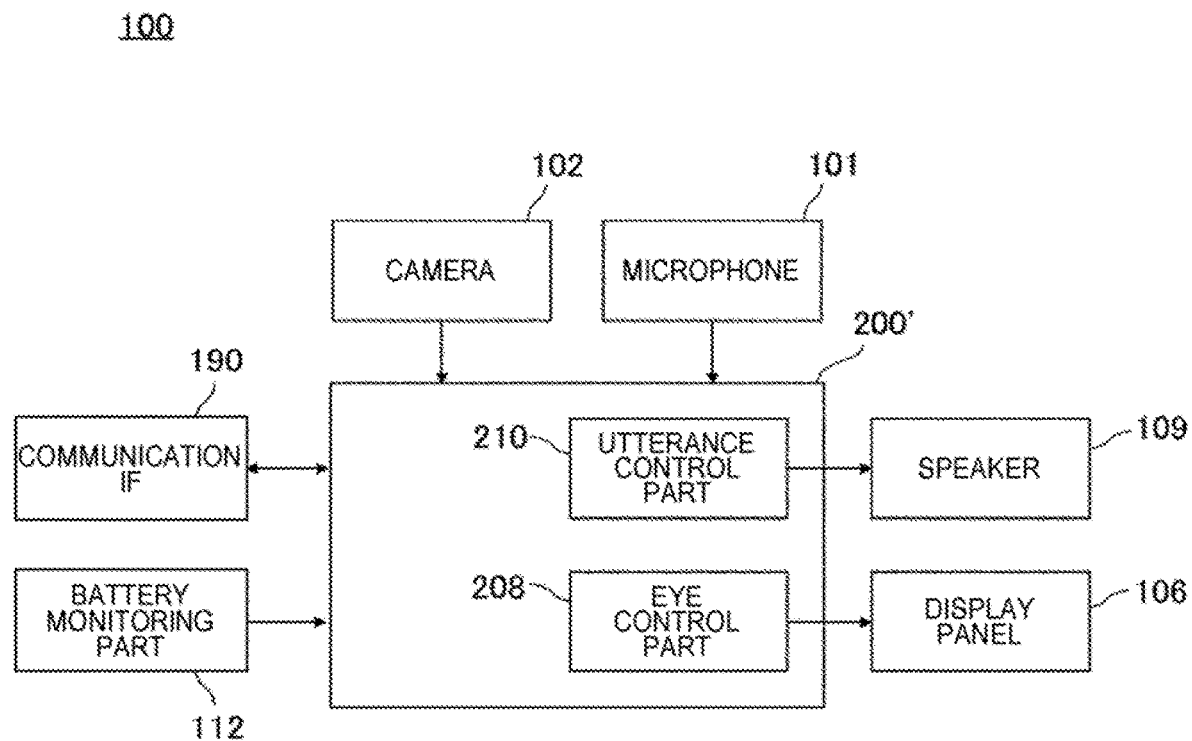
FIG. 13 is a system configuration diagram of a robot.

FIG. 13 is a system configuration diagram of the robot 100'. The same names are assigned to the elements which basically have the same functions as the elements described in the first embodiment. The description of the functions of the elements will be omitted unless otherwise specifically mentioned.

The robot 100' mainly includes the microphone 101, the camera 102, the display panel 106, the speaker 109, the battery monitoring part 112, a communication IF 190, and a control part 200'. The control part 200' is formed of, for example, a CPU, and also operates as a function execution part for executing each function. The control part 200' mainly operates as the eye control part 208 and the utterance control part 210.

The communication IF 190 is a communication interface for exchanging control signals and data with the server 300, and is, for example, a wireless LAN unit. The control part 200' transmits a voice signal received from the microphone 101 and an image signal received from the camera 102 to the server 300 via the communication IF 190. Furthermore, the eye control part 208 converts image data received from the expression selection part 207 via the communication IF 190 into an image signal that can be displayed on the display panel 106, and delivers the image signal to the display panel 106. The utterance control part 210 converts utterance data received from the voice selection part 209 via the communication IF 190 into a voice signal and delivers the voice signal to the speaker 109.

Even in such a system configuration of the second embodiment, as with the first embodiment, communication with the user can be realized. Further, by integrating the functions related to the calculation into the server 300, it is possible to facilitate configuration of the robot 100', and smooth communication can be realized without installing a high-performance control chip in the robot 100'. In addition, when the server 300 is responsible for arithmetic functions, the server 300 can also sequentially respond to arithmetic requests from a plurality of robots 100'. This makes it possible to reduce the manufacturing cost of the entire system.

Figure 14:
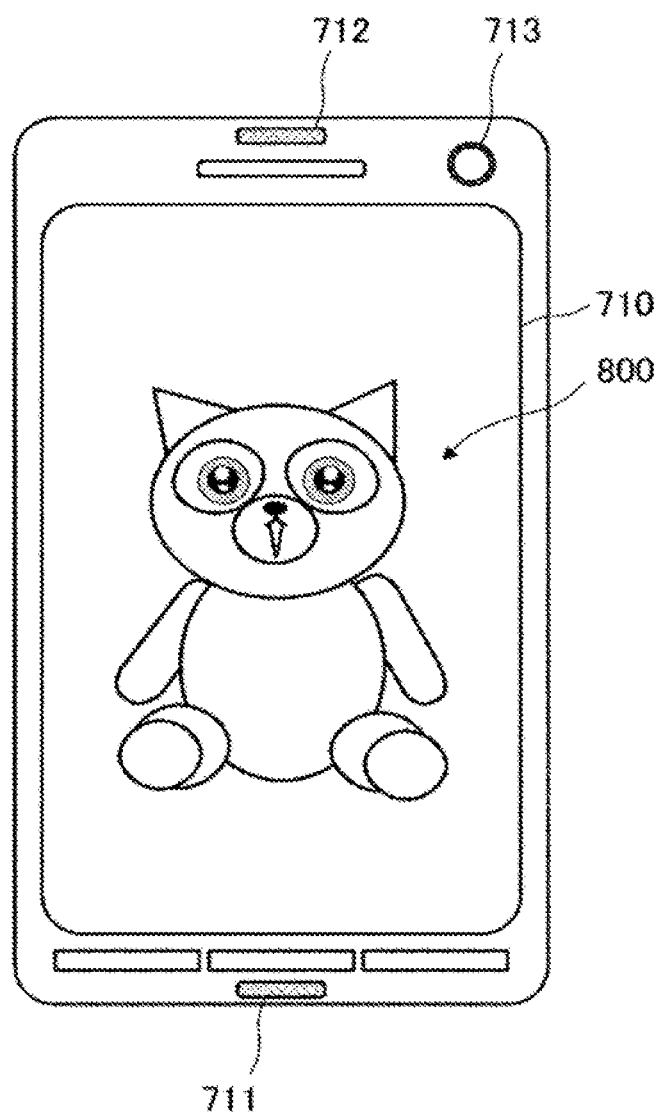
FIG. 14 is a schematic diagram of a tablet terminal according to a third embodiment.

Next, a third embodiment will be described. FIG. 14 is a schematic diagram of a tablet terminal 700 according to the third embodiment. In the first embodiment and the second embodiment, the robot 100 or 100' embodying a character is used as a partner with which the user talks. However, in the third embodiment, an image character 800 displayed on the tablet terminal 700 is used as a partner to talk with. If a character is realized as a robot, the user may feel the robot is like a pet and may have more of an attachment. However, it is possible for the tablet terminal 700 to more easily express a character.

The system configuration of the tablet terminal 700 is almost the same as the system configuration of the robot 100 of the first embodiment described with reference to FIG. 2. A description of similar configurations will be omitted, and different configurations will be described below.

The tablet terminal 700 includes a display panel 710, a microphone 711, a speaker 712, and a camera 713. The display panel 710 is, for example, a liquid crystal panel, and displays the image character 800. Therefore, the tablet terminal 700 does not include the display panel 106 for displaying only the image of the eye in the first embodiment.

The microphone 711 is an element replacing the microphone 101 of the first embodiment. The microphone 711 collects a user's uttered voice. The speaker 712 is an element replacing the speaker 109 of the first embodiment. The speaker 712 receives a voice signal converted by the utterance control part 210, and outputs a response voice. The camera 713 is an element replacing the camera 102 of the first embodiment. The camera 713 captures an image of a face of the user facing the tablet terminal 700.

The tablet terminal 700 may not only change an expression of the eyes but also express an emotion with an entire face or even an entire body. In that case, the response expression DB 320 may be configured to store image data corresponding to the entire face and the entire body in association with a type and degree of each emotion.

In this way, when the tablet terminal 700 is made to function as a communication device, dedicated hardware as a communication device is not required. Therefore, the user can more easily enjoy dialogue with the character. In addition, when the communication device has a configuration that allows the user to talk with the image character 800 in conjunction with another application of the tablet terminal 700, the communication device can be applied to various purposes.

Next, some modifications will be described. In the first embodiment, the robot 100 is provided with substantially all the configurations. In the second embodiment, the arithmetic processing part 400 of the server 300 is responsible for the principal calculation. However, in a system in which a robot and a server cooperate with each other, each of the robot and the server may have an arithmetic processing part and may share functions to be carried out. For example, the arithmetic processing part at the robot side may be responsible for a minor arithmetic operation, and the arithmetic processing part at the server side may be responsible for a heavy arithmetic operation that requires analysis. Specifically, the arithmetic processing part at the robot side may be responsible for a nodding behavior or a question sentence issued from the robot side, and the arithmetic processing part at the server side may be responsible for a user's personal authentication, emotion estimation, accumulation of dialogue data, and the like. In a case of adopting such a configuration, the system in which the robot and the server cooperate with each other is a communication device.

Furthermore, the disclosure is not limited to a system in which the robot and the server cooperate with each other, but may be applied to a system in which the tablet terminal described in the third embodiment or a smartphone and a server cooperate with each other. Even with such a configuration, the arithmetic processing part at the tablet terminal side or at the smartphone side may be responsible for a minor arithmetic operation, and the arithmetic processing part at the server side may be responsible for a heavy arithmetic operation that requires analysis. In a case of adopting such a configuration, the system in which the tablet terminal or the smartphone and the server cooperate with each other is a communication device.

In each of the above-described embodiments, the camera captures an image of a face of a user as a partner of a dialog. However, an angle of view may be adjusted so as to capture an image of an entire body of the user. For example, when a state of the entire body in jumping or hunching can be observed, it is possible to estimate the second emotion more accurately. The above-described embodiments have described, as an information source for estimating the second emotion, a face and biological information of the user who is talking. However, the disclosure is not limited thereto. Various kinds of information other than the user's utterance information may be an information source for estimating the second emotion. For example, when a microphone for collecting a sound from the surrounding environment is provided, it is possible to collect a voice unexpectedly uttered from a person other than a user as a part of the dialog. The second emotion estimation part 204 can estimate an emotion of "surprised" depending on a level of unexpectedness.

As a sensor for acquiring information on the surrounding environment, it is possible to adopt sensors other than a sound-collecting microphone. For example, when a temperature sensor or a humidity sensor is used as the sensor for acquiring the information on the surrounding environment, the second emotion estimation part 204 may use output signals of these sensors as information for estimating a degree of discomfort of the user.

In each of the above-described embodiments, a Russell's circumplex model is used for calculating the empathetic emotion. By using the Russell's circumplex model, it is possible to calculate the user's emotion more quantitatively. However, in computing empathetic emotions, other various known techniques may be adopted for calculating the empathetic emotion.

What is claimed is:

1. A communication device that allows a character to talk with a user, the communication device comprising:
    circuitry configured to:
    acquire an utterance of the user to the character;
    acquire information different from the utterance;
    generate a response voice to be emitted by the character based on a content of the utterance;
    generate a first response expression to be expressed by a face portion of the character based on a first emotion estimated based on the content of the utterance and a second emotion estimated based on the information different from the utterance; and
    generate a second response expression to be expressed by the face portion of the character based on the first emotion without using the second emotion,
    wherein the first response expression is different from the second response expression.

2. The communication device according to claim 1, further comprising:
    a database configured to store a plurality of response expressions associated with a plurality of emotions, respectively,
    wherein the circuitry is configured to select, from the database, a response expression associated with a third emotion that is determined according to a combination of the first emotion and the second emotion as the first response expression.

3. The communication device according to claim 2, wherein:
    in the database, the plurality of emotions are associated with the plurality of the response expressions, respectively, based on a Russell's circumplex model; and
    the circuitry is configured to determine the third emotion based on a sum of a first vector corresponding to the first emotion in the Russell's circumplex model and a second vector corresponding to the second emotion in the Russell's circumplex model.

4. The communication device according to claim 2, wherein the circuitry is configured to select, from the database, a response expression corresponding to a fourth emotion that approximates the third emotion in a predetermined range as the first response expression.

5. The communication device according to claim 1, wherein when generating two response expressions consecutively, the circuitry is configured to generate at least one interpolation response expression between the two response expressions, the at least one interpolation response expression interpolating the two response expressions.

6. The communication device according to claim 1, further comprising an imaging part sensor configured to capture an image of the user.

7. The communication device according to claim 1, further comprising a biometric sensor configured to acquire biological information of the user.

8. The communication device according to claim 1, wherein the information acquisition part includes further comprising an environmental sensor configured to acquire environmental information of a surrounding environment of the communication device.

9. The communication device according to claim 1, further comprising:
    a state acquisition sensor configured to acquire an internal state of a character device that embodies the character,
    wherein the circuitry is configured to generate the first response expression based on the internal state.

10. A communication robot, comprising:
    the communication device according to claim 1; and
    the face portion configured to express the first and second response expressions.

11. A non-transitory computer-readable storage medium, comprising:
    a memory configured to store a communication control program to be executed by a computer of a communication device that allows a character to talk with a user,
    wherein when the communication control program is executed by the computer, the computer executes:
    acquiring an utterance of the user to the character;
    acquiring information different from the utterance;
    generating a response voice to be emitted by the character based on a content of the utterance;
    generating a first response expression to be expressed by a face portion of the character based on a first emotion estimated based on the content of the utterance and a second emotion estimated based on the information different from the utterance; and
    generating a second response expression to be expressed by the face portion of the character based on the first emotion without using the second emotion,
    wherein the first response expression is different from the second response expression.

* * * * *